United States Patent
Ajemba et al.

(10) Patent No.: US 12,423,490 B2
(45) Date of Patent: Sep. 23, 2025

(54) MODEL MOSAIC FRAMEWORK FOR MODELING GLUCOSE SENSITIVITY

(71) Applicant: MEDTRONIC MINIMED, INC., Northridge, CA (US)

(72) Inventors: Peter Ajemba, Canyon Country, CA (US); Keith Nogueira, Mission Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1012 days.

(21) Appl. No.: 17/163,233

(22) Filed: Jan. 29, 2021

(65) Prior Publication Data

US 2022/0245306 A1 Aug. 4, 2022

(51) Int. Cl.
| | | |
|---|---|---|
| A61B 5/145 | (2006.01) | |
| G06F 30/27 | (2020.01) | |
| G16H 10/40 | (2018.01) | |
| G16H 50/20 | (2018.01) | |
| G16H 50/50 | (2018.01) | |

(52) U.S. Cl.
CPC ............. *G06F 30/27* (2020.01); *G16H 10/40* (2018.01); *G16H 50/20* (2018.01); *G16H 50/50* (2018.01)

(58) Field of Classification Search
None
See application file for complete search history.

(56) References Cited

U.S. PATENT DOCUMENTS

| | | |
|---|---|---|
| 4,562,751 A | 1/1986 | Nason et al. |
| 4,573,994 A | 3/1986 | Fischell et al. |
| 4,678,408 A | 7/1987 | Nason et al. |
| 4,685,903 A | 8/1987 | Cable et al. |
| 4,755,173 A | 7/1988 | Konopka et al. |
| 5,391,250 A | 2/1995 | Cheney, II et al. |
| 5,482,473 A | 1/1996 | Lord et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |

(Continued)

OTHER PUBLICATIONS

International Search Report and Written Opinion dated May 9, 2022, in Application No. PCT/US2022/014253.

(Continued)

*Primary Examiner* — Aurelie H Tu
(74) *Attorney, Agent, or Firm* — Weaver Austin Villeneuve & Sampson LLP

(57) ABSTRACT

Methods, systems, and devices for modeling a relationship between glucose sensitivity and a sensor electrical property are described herein. More particularly, the methods, systems, and devices describe partitioning an input signal feature space relating glucose sensitivity and a sensor electrical property into subspaces and training a model for each subspace. For example, the subspace models may form a mosaic of models, for which the output is more accurate than a single model.

20 Claims, 12 Drawing Sheets

(56) References Cited

U.S. PATENT DOCUMENTS

| | | |
|---|---|---|
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 12,114,972 B2 | 10/2024 | Mallas et al. |
| 2004/0087844 A1* | 5/2004 | Yen ............... A61B 5/1455 600/319 |
| 2007/0123819 A1 | 5/2007 | Memoe et al. |
| 2008/0214910 A1 | 9/2008 | Buck |
| 2010/0160861 A1 | 6/2010 | Causey, III et al. |
| 2017/0169180 A1 | 6/2017 | Hamann et al. |
| 2018/0242015 A1 | 8/2018 | Katsavounidis |
| 2019/0192768 A1 | 6/2019 | Gupta et al. |
| 2020/0170508 A1 | 6/2020 | Garcia et al. |
| 2020/0178868 A1 | 6/2020 | Mueller et al. |
| 2020/0237271 A1 | 7/2020 | Vanslyke et al. |
| 2020/0245910 A1 | 8/2020 | Mallas et al. |
| 2021/0007607 A1 | 1/2021 | Frank et al. |
| 2021/0209497 A1 | 7/2021 | Wang et al. |
| 2021/0369149 A1 | 12/2021 | Böhm et al. |
| 2022/0039702 A1 | 2/2022 | Wu et al. |
| 2022/0233108 A1 | 7/2022 | Ajemba et al. |
| 2022/0240818 A1 | 8/2022 | Ajemba et al. |
| 2022/0313124 A1 | 10/2022 | Garcia et al. |
| 2023/0028587 A1 | 1/2023 | Scott et al. |
| 2025/0134416 A1 | 5/2025 | Nava-Guerra et al. |
| 2025/0134417 A1 | 5/2025 | Basilico et al. |

OTHER PUBLICATIONS

U.S. Non-Final office Action dated Nov. 15, 2022 in U.S. Appl. No. 17/163,273.

International Preliminary Report on Patentability and Written Opinion dated Aug. 10, 2023 in PCT Application No. PCT/US2022/014253.

Yu, X., et al., "Model-fusion-based Online Glucose Concentration Predictions in People With Type 1 Diabetes," Control Engineering Practice, 2018, vol. 71, pp. 129-141.

EP Extended European Search report dated Apr. 23, 2025 in EP Application No. 24208150.3.

EP Extended European Search report dated Mar. 26, 2025 in EP Application No. 24208161.0.

* cited by examiner

100

150

MODEL MOSAIC FRAMEWORK FOR MODELING GLUCOSE SENSITIVITY

FIELD

The present technology is generally related to sensor technology, including sensors used for sensing a variety of physiological parameters, e.g., glucose concentration.

BACKGROUND

Over the years, a variety of sensors have been developed for detecting and/or quantifying specific agents or compositions in a patient's blood, which enable patients and medical personnel to monitor physiological conditions within the patient's body. Illustratively, subjects may wish to monitor blood glucose levels in a subject's body on a continuing basis. Thus, glucose sensors have been developed for use in obtaining an indication of blood glucose levels in a diabetic patient. Such readings are useful in monitoring and/or adjusting a treatment regimen which typically includes the regular administration of insulin to the patient. Presently, a patient can measure his/her blood glucose ("BG") using a BG measurement device (i.e., glucose meter), such as a test strip meter, a continuous glucose measurement system (or a continuous glucose monitor), or a hospital BG test. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device.

SUMMARY

The relationship between glucose sensitivity and sensor features (e.g., sensor electrical properties) of sensor devices is essential to accurate modeling, as it affects whether a current continuous glucose monitoring ("CGM") system utilizes measurements from a sensor device or blank the sensor device (e.g., remove, ignore, or forego to transmit the sensor data to the sensor device or any other device with a display interface). However, a single model is often unable to accurately depict this complex relationship. For example, sensor electrical properties such as time, wear, battery, calibration, and other properties can affect glucose sensitivity in complex ways that are difficult to capture with a single model. Additionally, glucose sensitivity may vary as sensor features change, for example, due to variability in the sensing environment, physiological dynamics, or sensor manufacturing. Methods and systems described herein partition an input signal feature space into a plurality of contiguous subspaces. The system selects and trains a model for each subspace from a plurality of types of models. Such input signal feature space partitioning is often unsuccessful in conjunction with current systems. In fact, input signal feature space partitioning often leads to significant decreases in accuracy and performance due to a decrease in data available within each space. However, the methods and systems described herein utilize smart partitioning and training techniques in order to generate an accurate model. The resulting mosaic model is more accurate than a single model for determining the relationship between glucose sensitivity and a sensor electrical property of a sensor device.

The accuracy of this modeling technique improves upon the ability of the CGM system to comply with government standards of sensor devices. Government agencies (e.g., the Federal Drug Administration ("FDA")) impose restrictions and requirements for the sensitivity and accuracy of CGMs. For example, CGM devices are required to meet numerous criteria (e.g., FDA's integrated continuous glucose monitoring ("iCGM") criteria) in order for the sensor data to be considered accurate. In order to comply with the iCGM criteria, the CGM system must accurately model the relationship between glucose sensitivity and sensor electrical properties of a sensor device. The system may use the output of the mosaic of models to determine if the sensor device meets the iCGM standards. If the system determines that the sensor device is compliant with the iCGM criteria, the system may utilize readings from the sensor device. If the system determines that the sensor device is not compliant with the iCGM criteria, the system may blank the sensor data from a user device (e.g., remove, ignore, or forego to transmit the sensor data to the sensor device or any other device with a display interface). Thus, the methods, systems, and devices described herein allow for improved CGM techniques that are compatible with the FDA's iCGM criteria.

More particularly, the methods, systems, and devices describe partitioning an input signal feature space into a plurality of contiguous subspaces. For example, the input signal feature space may relate glucose sensitivity and a sensor electrical property (e.g., wear, time, battery life, calibration, etc.) associated with a sensor device. The system may train a machine learning model for each subspace to determine glucose sensitivity based on a range of values associated with the sensor electrical property for the subspace. In some embodiments, the machine learning model may take as inputs sensor data from the sensor device and may use training data as feedback. The training data may include clinical data on glucose sensitivity. In some embodiments, the system may also receive sensor data (e.g., relating to wear time, battery life, calibration, electrical data, or other sensor properties) associated with the sensor device from the sensor device. The system may input the sensor data into the machine learning model and may receive an output from the machine learning model indicating glucose sensitivity.

With input signal feature space division, discrepancies may arise at the boundaries between subspaces. For example, the separate models of adjacent subspaces may not align precisely, leading to gaps in the mosaic model. Therefore, methods and systems described herein detail smoothing and blending methods for correcting discrepancies between models. For example, the system may extend the model for each subspace into the adjacent subspaces. Therefore, the area surrounding the boundaries of the subspaces may comprise several overlapping models. In some embodiments, the system may build a composite model based on the models of the entire input signal feature space. The system may overlay the composite model on top of the models of each subspace (e.g., overlaying the entire input signal feature space) and blend the composite model with the models of each subspace. In some embodiments, the system may use other methods of smoothing or blending the glucose sensitivity outputs at the subspace boundaries in order to generate an accurate and smooth mosaic model.

In some aspects, methods, systems, and devices for continuous glucose monitoring are described. For example, the system may partition an input signal feature space into a plurality of contiguous subspaces, the input signal feature space relating glucose sensitivity and a sensor electrical property associated with a sensor device. In some embodiments, for each subspace, the system may train the machine learning model to predict glucose sensitivity based on a range of values associated with the sensor electrical property for the subspace. In some embodiments, the system may train the machine learning model using training data that includes clinical data on glucose sensitivity. The system may receive sensor data from the sensor device and may input the sensor data into the machine learning model. The system may receive an output from the machine learning model indicating glucose sensitivity. In some embodiments, the system may determine whether to blank the sensor device (e.g., remove, ignore, or forego to transmit the sensor data to the sensor device or any other device with a display interface) based on the output from the machine learning model.

Various other aspects, features, and advantages will be apparent through the detailed description and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a sub-part of, or the entirety of, a given item (e.g., data) unless the context clearly dictates otherwise.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION

Figure 1:
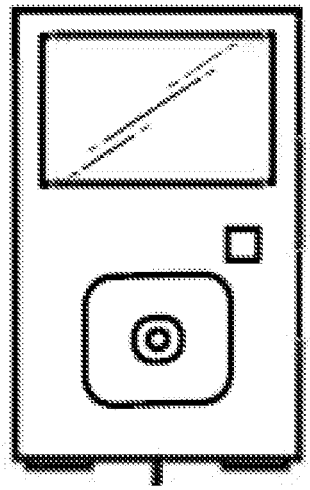
FIG. 1 illustrates wearable sensor electronics devices, in accordance with one or more embodiments.
Figure 1:
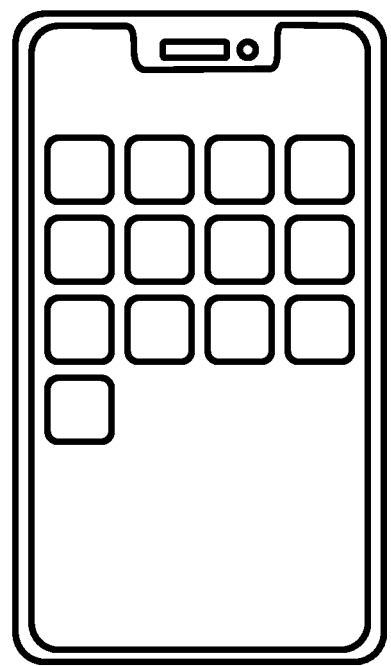

In the following description, reference is made to the accompanying drawings which form a part hereof and which illustrate several embodiments of the present inventions. It is understood that other embodiments may be utilized, and structural and operational changes may be made without departing from the scope of the present inventions.

The inventions herein are described below with reference to flowchart illustrations of methods, systems, devices, apparatus, and programming and computer program products. It will be understood that each block of the flowchart illustrations, and combinations of blocks in the flowchart illustrations, can be implemented by programing instructions, including computer program instructions (as can any menu screens described in the figures). These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein. Programming instructions may also be stored in and/or implemented via electronic circuitry (e.g., storage circuitry, processing circuitry), including integrated circuits (ICs) and Application Specific Integrated Circuits (ASICs) used in conjunction with sensor devices, apparatuses, and systems. The following terms and definitions may also be used herein:

| Term | Definition |
| --- | --- |
| BG | Blood Glucose value in mg/dL typically from a fingerstick reading. Assumed use is for a sensor calibration |
| Calibrated Mode | Sensor operation mode in which the algorithm expects to receive BG calibrations as part of regular operation |
| CE | Calibration Error |
| CF (or calFactor) | Calibration Factor, sensor sensitivity to glucose used to calculate sensor glucose. Units are mg/dL/nA |
| CR (or cr) | Calibration Ratio, sensitivity based on a |

-continued

| Term | Definition |
| --- | --- |
| | single BG and Isig |
| Discard | Packet flagged to be invalid based on Isig. |
| early calibration | Temporary CF update on the packet following a BG |
| EIS | Electrochemical Impedance Spectroscopy, Diagnostic capability to measure impedances at varying frequencies applied by the AFE IC |
| final calibration | Refers to updates to CF and other variables which may occur 10-15 minutes after a BG entry |
| fisig | Filtered Isig, used in calibration and SG calculation |
| GST | Glucose Sensor Transmitter |
| GOx | Glucose Oxidase |
| initialization | Sensor Initialization. This typically refers to data collection activities during sensor warm up period |
| Instant calibration error | CE check based on prior Isig, determines if a BG can be used for calibration |
| invalid packet | Refers to a packet being flagged as invalid. Packets flagged as invalid do not show SG to the user. |
| Isig | 5-minute reading of sensor current in nA. Sometimes called "raw Isig" |
| Isig1 | 1-minute reading of sensor current in nA. Sometimes called "1-minute Isig" |
| Isig Dip | Isig Dip Calibration. Refers to logic which may adjust CF following a calibration on an abnormally low Isig |
| MAX_CR | Maximum acceptable CR |
| MIN_CR | Minimum acceptable CR |
| Not Calibrated Mode | Sensor operation mode in which the algorithm does not expect to receive BG calibrations as part of regular operations. The algorithm can utilize BG calibrations if any is made available. |
| Packet (or SG Packet or Isig Packet) | Refers to the collection of variables calculated at the 5-minute interval, including Isig, sg, etc. |
| SG | Sensor Glucose value in mg/dL |
| Vset | Voltage potential |

FIG. 1 illustrates wearable sensor electronics devices 100 and 150, in accordance with one or more embodiments. In some embodiments, wearable sensor electronics device 100 may be an infusion pump. In some embodiments, the infusion pump may include a display. In some embodiments, wearable sensor electronics device 100 may be a combination infusion pump/glucose sensor. In some embodiments, wearable sensor electronics device 150 may be a cellular phone or any computing device. In some embodiments, wearable sensor electronics devices 100 and 150 may include a computer, a personal digital assistant, a pager, or any other suitable wearable device. In some embodiments, wearable sensor electronics devices 100 and 150 may house components described below in relation to FIGS. 2-6.

Figure 2:
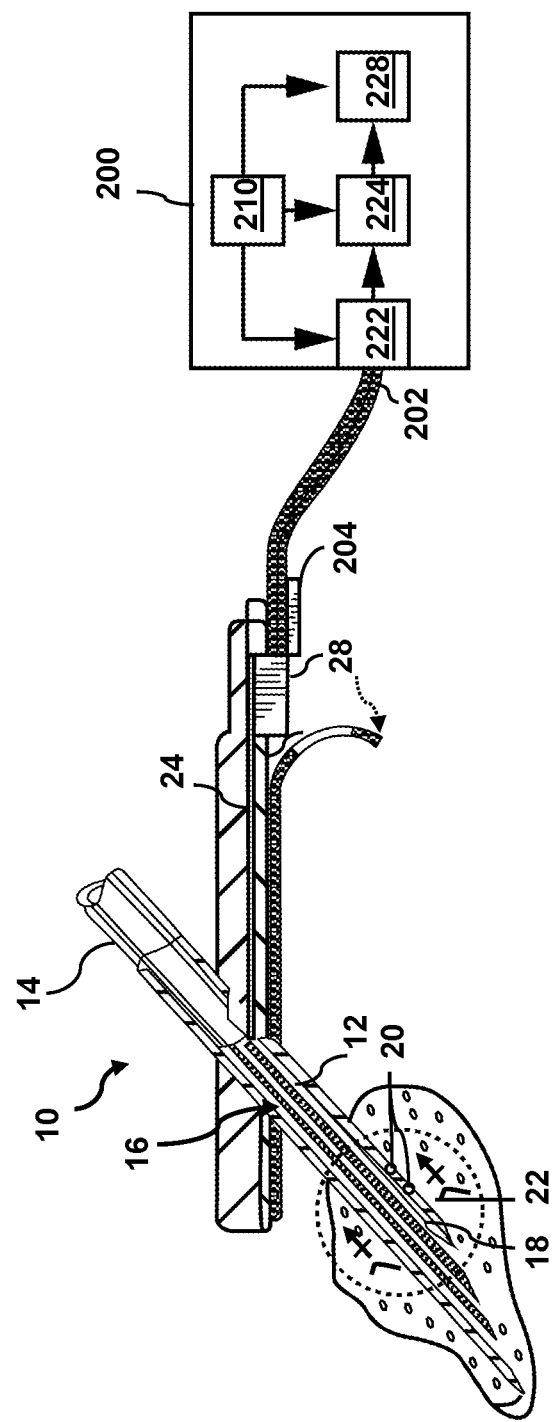
FIG. 2 is a perspective view of a subcutaneous sensor insertion set and block diagram of a sensor electronics device, in accordance with one or more embodiments.

FIG. 2 is a perspective view of a subcutaneous sensor insertion set and a block diagram of a sensor electronics device (e.g., wearable sensor electronics devices 100 or 150, as shown in FIG. 1, or any other suitable sensor electronics device). As illustrated in FIG. 2, a subcutaneous sensor set 10 is provided for subcutaneous placement of an active portion of a flexible sensor 12 (see, e.g., FIG. 3), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In one embodiment, the one or more sensor electrodes 20 may include a counter electrode, a reference electrode, and one or more working electrodes. After insertion, the insertion needle 14 is withdrawn to leave the cannula 16 with the sensing portion 18 and the sensor electrodes 20 in place at the selected insertion site.

In particular embodiments, the subcutaneous sensor set 10 facilitates accurate placement of a flexible thin film electrochemical sensor 12 of the type used for monitoring specific blood parameters representative of a user's condition. The sensor 12 monitors glucose levels in the body and may be used in conjunction with automated or semi-automated medication infusion pumps (e.g., wearable sensor electronics device 100, as shown in FIG. 1) of the external or implantable type to control delivery of insulin to a diabetic patient, as described, e.g., in U.S. Pat. Nos. 4,562,751; 4,678,408; 4,685,903 or 4,573,994, which are herein incorporated by reference.

Particular embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor or sensor electronics device 200 (e.g., wearable sensor electronics devices 100 or 150, as shown in FIG. 1, or any other suitable sensor electronics device) for monitoring a user's condition in response to signals derived from the sensor electrodes 20. Further description of flexible thin film sensors of this general type are to be found in U.S. Pat. No. 5,391,250, entitled METHOD OF FABRICATING THIN FILM SENSORS, which is herein incorporated by reference. The connection portion 24 may be conveniently connected electrically to the monitor or sensor electronics device 200 or by a connector block 28 (or the like) as shown and described in U.S. Pat. No. 5,482,473, entitled FLEX CIRCUIT CONNECTOR, which is also herein incorporated by reference. Thus, in accordance with some embodiments, subcutaneous sensor sets 10 may be configured or formed to work with either a wired or a wireless characteristic monitor system.

The sensor electrodes 20 may be used in a variety of sensing applications and may be configured in a variety of ways. For example, the sensor electrodes 20 may be used in physiological parameter sensing applications in which some type of biomolecule is used as a catalytic agent. For example, the sensor electrodes 20 may be used in a glucose and oxygen sensor having a glucose oxidase (GOx) enzyme catalyzing a reaction with the sensor electrodes 20. The sensor electrodes 20, along with a biomolecule or some other catalytic agent, may be placed in a human body in a vascular or non-vascular environment. For example, the sensor electrodes 20 and biomolecule may be placed in a vein and be subjected to a blood stream or may be placed in a subcutaneous or peritoneal region of the human body.

The monitor 200 may also be referred to as a sensor electronics device 200. The monitor 200 may include a power source 210, a sensor interface 222, processing electronics 224, and data formatting electronics 228. The monitor 200 may be coupled to the sensor set 10 by a cable 202 through a connector that is electrically coupled to the connector block 28 of the connection portion 24. In an alternative embodiment, the cable may be omitted. In this embodiment, the monitor 200 may include an appropriate connector for direct connection to the connection portion 204 of the sensor set 10. The sensor set 10 may be modified to have the connector portion 204 positioned at a different location, e.g., on top of the sensor set to facilitate placement of the monitor 200 over the sensor set.

In one embodiment, the sensor interface 222, the processing electronics 224, and the data formatting electronics 228 are formed as separate semiconductor chips, however, alternative embodiments may combine the various semiconductor chips into a single, or multiple customized semiconductor chips. The sensor interface 222 connects with the cable 202 that is connected with the sensor set 10.

The power source 210 may be a battery. The battery can include three series silver oxide 357 battery cells. In alternative embodiments, different battery chemistries may be utilized, such as lithium-based chemistries, alkaline batteries, nickel metal hydride, or the like, and a different number of batteries may be used. The monitor 200 provides power to the sensor set via the power source 210, through the cable 202 and cable connector 204. In one embodiment, the power is a voltage provided to the sensor set 10. In another embodiment, the power is a current provided to the sensor set 10. In an embodiment, the power is a voltage provided at a specific voltage to the sensor set 10.

Figure 3:
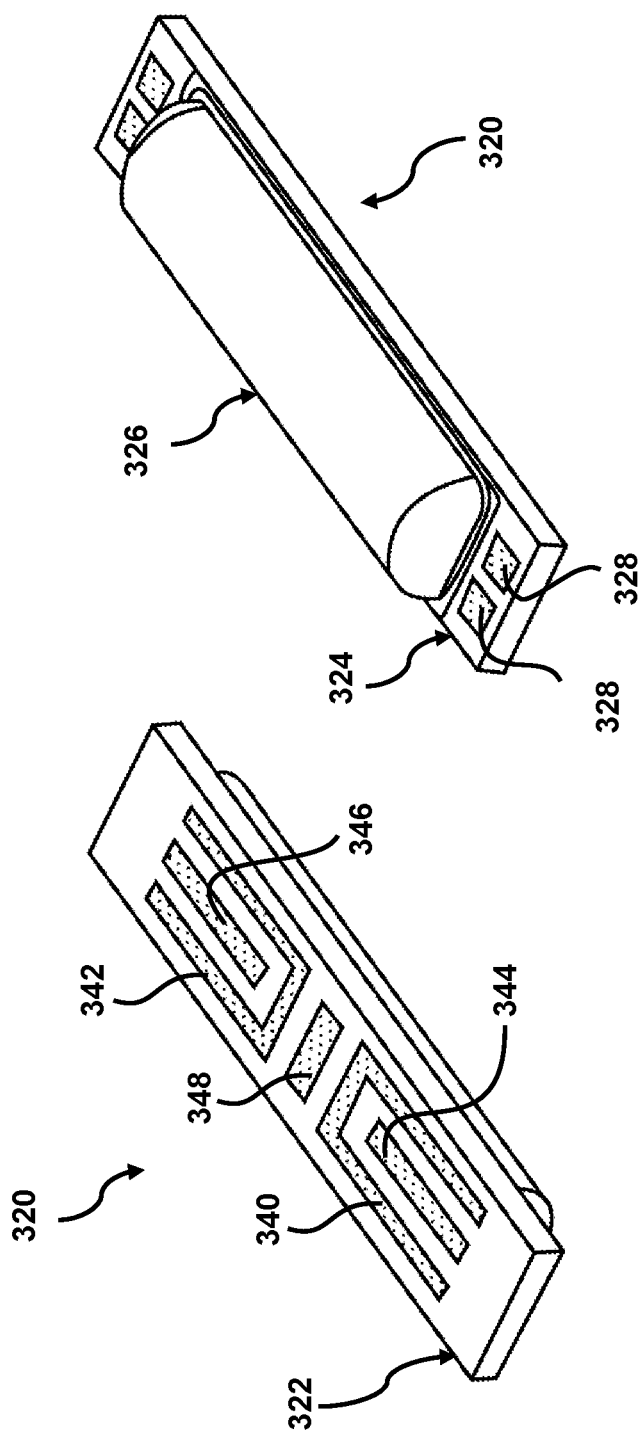
FIG. 3 illustrates a substrate having two sides, a first side which contains an electrode configuration and a second side which contains electronic circuitry, in accordance with one or more embodiments.

FIG. 3 illustrates an implantable sensor, and electronics for driving the implantable sensor in accordance with one embodiment. FIG. 3 shows a substrate 320 having two sides, a first side 322 of which contains an electrode configuration and a second side 324 of which contains electronic circuitry (e.g., storage circuitry, processing circuitry, etc.). As may be seen in FIG. 3, a first side 322 of the substrate comprises two counter electrode-working electrode pairs 340, 342, 344, 346 on opposite sides of a reference electrode 348. A second side 324 of the substrate comprises electronic circuitry. As shown, the electronic circuitry may be enclosed in a hermetically sealed casing 326, providing a protective housing for the electronic circuitry. This allows the sensor substrate 320 to be inserted into a vascular environment or other environment which may subject the electronic circuitry to fluids. By sealing the electronic circuitry in a hermetically sealed casing 326, the electronic circuitry may operate without risk of short circuiting by the surrounding fluids. Also shown in FIG. 3 are pads 328 to which the input and output lines of the electronic circuitry may be connected. The electronic circuitry itself may be fabricated in a variety of ways. According to an embodiment, the electronic circuitry may be fabricated as an integrated circuit using techniques common in the industry.

Figure 4:
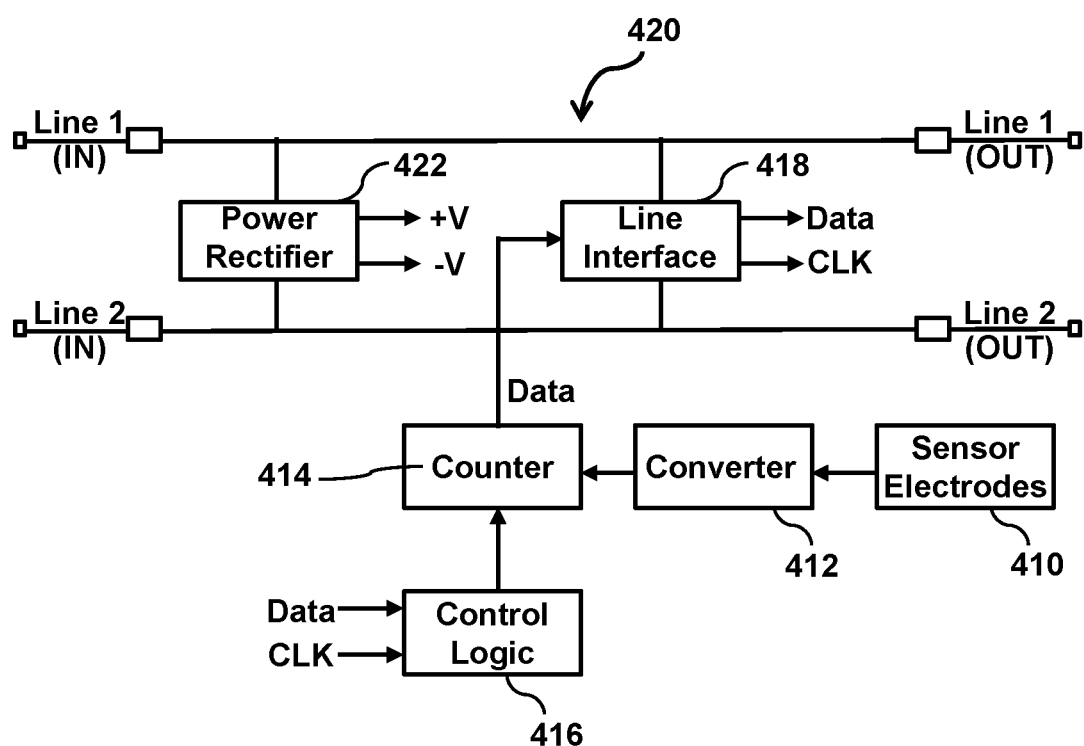
FIG. 4 illustrates a block diagram of a sensor electronics device and a sensor including a plurality of electrodes, in accordance with one or more embodiments.

FIG. 4 illustrates a general block diagram of an electronic circuit for sensing an output of a sensor according to one embodiment. At least one pair of sensor electrodes 410 may interface to a data converter 412, the output of which may interface to a counter 414. The counter 414 may be controlled by control logic 416. The output of the counter 414 may connect to a line interface 418. The line interface 418 may be connected to input and output lines 420 and may also connect to the control logic 416. The input and output lines 420 may also be connected to a power rectifier 422.

The sensor electrodes 410 may be used in a variety of sensing applications and may be configured in a variety of ways. For example, the sensor electrodes 410 may be used in physiological parameter sensing applications in which some type of biomolecule is used as a catalytic agent. For example, the sensor electrodes 410 may be used in a glucose and oxygen sensor having a GOx enzyme catalyzing a reaction with the sensor electrodes 410. The sensor electrodes 410, along with a biomolecule or some other catalytic agent, may be placed in a human body in a vascular or non-vascular environment. For example, the sensor electrodes 410 and biomolecule may be placed in a vein and be subjected to a blood stream.

Figure 5:
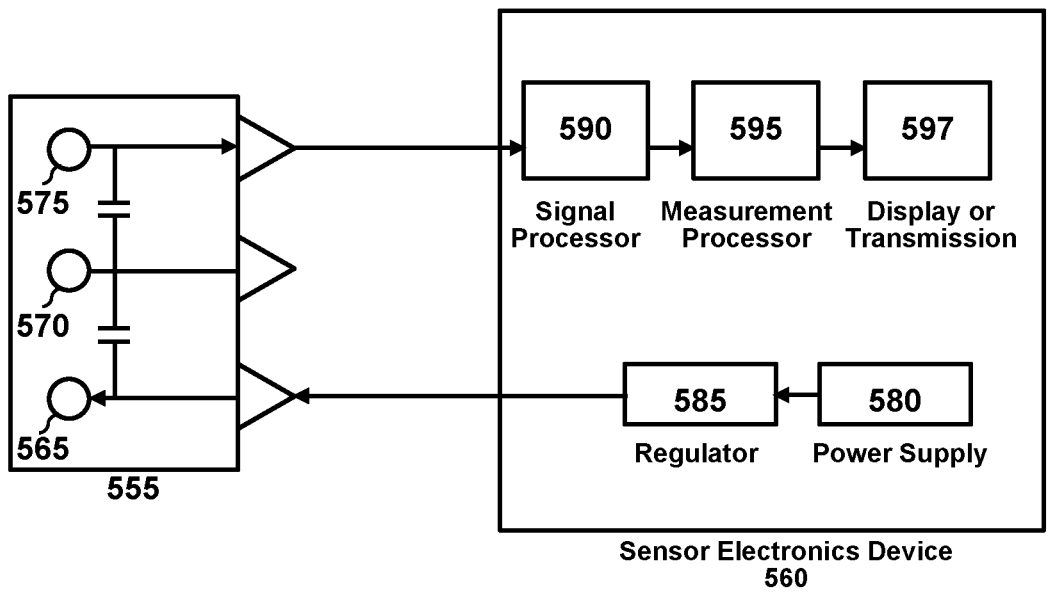
FIG. 5 illustrates an alternative embodiment of the invention including a sensor and a sensor electronics device, in accordance with one or more embodiments.
Figure 5:
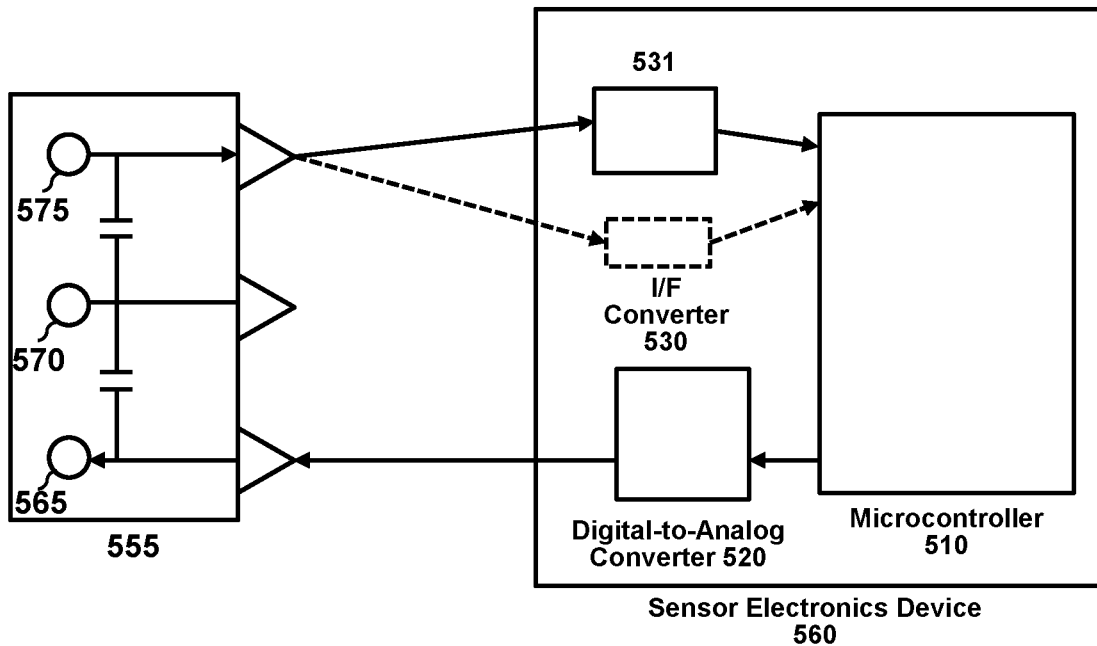

FIG. 5 illustrates a block diagram of a sensor electronics device (e.g., wearable sensor electronics devices 100 or 150, as shown in FIG. 1, or any other suitable sensor electronics device) and a sensor including a plurality of electrodes according to an embodiment herein. FIG. 5 includes system 500. System 500 includes a sensor 555 and a sensor electronics device 560. The sensor 555 includes a counter electrode 565, a reference electrode 570, and a working electrode 575. The sensor electronics device 560 includes a power supply 580, a regulator 585, a signal processor 590, a measurement processor 595, and a display/transmission module 597. The power supply 580 provides power (in the form of either a voltage, a current, or a voltage including a current) to the regulator 585. The regulator 585 transmits a regulated voltage to the sensor 555. In one embodiment, the regulator 585 transmits a voltage to the counter electrode 565 of the sensor 555.

The sensor 555 creates a sensor signal indicative of a concentration of a physiological characteristic being measured. For example, the sensor signal may be indicative of a blood glucose reading. In an embodiment utilizing subcutaneous sensors, the sensor signal may represent a level of hydrogen peroxide in a subject. In an embodiment where blood or cranial sensors are utilized, the amount of oxygen is being measured by the sensor and is represented by the sensor signal. In an embodiment utilizing implantable or long-term sensors, the sensor signal may represent a level of oxygen in the subject. The sensor signal is measured at the working electrode 575. In one embodiment, the sensor signal may be a current measured at the working electrode. In an embodiment, the sensor signal may be a voltage measured at the working electrode.

The signal processor 590 receives the sensor signal (e.g., a measured current or voltage) after the sensor signal is measured at the sensor 555 (e.g., the working electrode). The signal processor 590 processes the sensor signal and generates a processed sensor signal. The measurement processor 595 receives the processed sensor signal and calibrates the processed sensor signal utilizing reference values. In one embodiment, the reference values are stored in a reference memory and provided to the measurement processor 595. The measurement processor 595 generates sensor measurements. The sensor measurements may be stored in a measurement memory (not shown) or by circuitry (e.g., storage circuitry). The sensor measurements may be sent to a display/transmission device to be either displayed on a display in a housing with the sensor electronics or transmitted to an external device.

The sensor electronics device 560 may be a monitor which includes a display to display physiological characteristics readings. The sensor electronics device 560 may also be installed in a desktop computer, a pager, a television including communications capabilities, a laptop computer, a server, a network computer, a personal digital assistant (PDA), a portable telephone including computer functions, an infusion pump including a display (e.g., wearable sensor electronics device 100, as shown in FIG. 1), a glucose sensor including a display, and/or a combination infusion pump/glucose sensor (e.g., wearable sensor electronics device 100, as shown in FIG. 1). The sensor electronics device 560 may be housed in a blackberry (e.g., wearable sensor electronics device 150, as shown in FIG. 1), a network device, a home network device, or an appliance connected to a home network.

FIG. 5 also includes system 550. System 550 includes a sensor electronics device 560 and a sensor 555. The sensor includes a counter electrode 565, a reference electrode 570, and a working electrode 575. The sensor electronics device 560 includes a microcontroller 510 and a digital-to-analog converter (DAC) 520. The sensor electronics device 560 may also include a current-to-frequency converter (I/F converter) 530.

The microcontroller 510 includes software program code, which when executed, or programmable logic which, causes the microcontroller 510 to transmit a signal to the DAC 520, where the signal is representative of a voltage level or value that is to be applied to the sensor 555. The DAC 520 receives the signal and generates the voltage value at the level instructed by the microcontroller 510. In one embodiment, the microcontroller 510 may change the representation of the voltage level in the signal frequently or infrequently. Illustratively, the signal from the microcontroller 510 may instruct the DAC 520 to apply a first voltage value for one second and a second voltage value for two seconds.

The sensor 555 may receive the voltage level or value. In one embodiment, the counter electrode 565 may receive the output of an operational amplifier which has as inputs the reference voltage and the voltage value from the DAC 520. The application of the voltage level causes the sensor 555 to create a sensor signal indicative of a concentration of a physiological characteristic being measured. In an embodiment, the microcontroller 510 may measure the sensor signal (e.g., a current value) from the working electrode. Illustratively, a sensor signal measurement circuit 531 may measure the sensor signal. In an embodiment, the sensor signal measurement circuit 531 may include a resistor and the current may be passed through the resistor to measure the value of the sensor signal. In an embodiment, the sensor signal may be a current level signal and the sensor signal measurement circuit 531 may be a current-to-frequency (I/F) converter 530. The current-to-frequency converter 530 may measure the sensor signal in terms of a current reading, convert it to a frequency-based sensor signal, and transmit the frequency-based sensor signal to the microcontroller 510. In some embodiments, the microcontroller 510 may be able to receive frequency-based sensor signals easier than non-frequency-based sensor signals. The microcontroller 510 receives the sensor signal, whether frequency-based or non-frequency-based, and determines a value for the physiological characteristic of a subject, such as a blood glucose level. The microcontroller 510 may include program code, which when executed or run, is able to receive the sensor signal and convert the sensor signal to a physiological characteristic value. In one embodiment, the microcontroller 510 may convert the sensor signal to a blood glucose level. In an embodiment, the microcontroller 510 may utilize measurements stored within an internal memory or by circuitry (e.g., storage circuitry) in order to determine the blood glucose level of the subject. In an embodiment, the microcontroller 510 may utilize measurements stored within a memory external to the microcontroller 510 or by circuitry to assist in determining the blood glucose level of the subject.

After the physiological characteristic value is determined by the microcontroller 510, the microcontroller 510 may store measurements of the physiological characteristic values for a number of time periods. For example, a blood glucose value may be sent to the microcontroller 510 from the sensor in intervals (e.g., every second or five seconds), and the microcontroller may save sensor measurements in intervals (e.g., for five minutes or ten minutes of BG readings). The microcontroller 510 may transfer the measurements of the physiological characteristic values to a display on the sensor electronics device 560. For example, the sensor electronics device 560 may be a monitor which includes a display that provides a blood glucose reading for a subject. In one embodiment, the microcontroller 510 may transfer the measurements of the physiological characteristic values to an output interface of the microcontroller 510. The output interface of the microcontroller 510 may transfer the measurements of the physiological characteristic values, e.g., blood glucose values, to an external device, e.g., an infusion pump (e.g., wearable sensor electronics device 100, as shown in FIG. 1), a combined infusion pump/glucose meter (e.g., wearable sensor electronics device 100, as shown in FIG. 1), a computer, a personal digital assistant, a pager, a network appliance, a server, a cellular phone (e.g., wearable sensor electronics device 150, as shown in FIG. 1), or any computing device.

Figure 6:
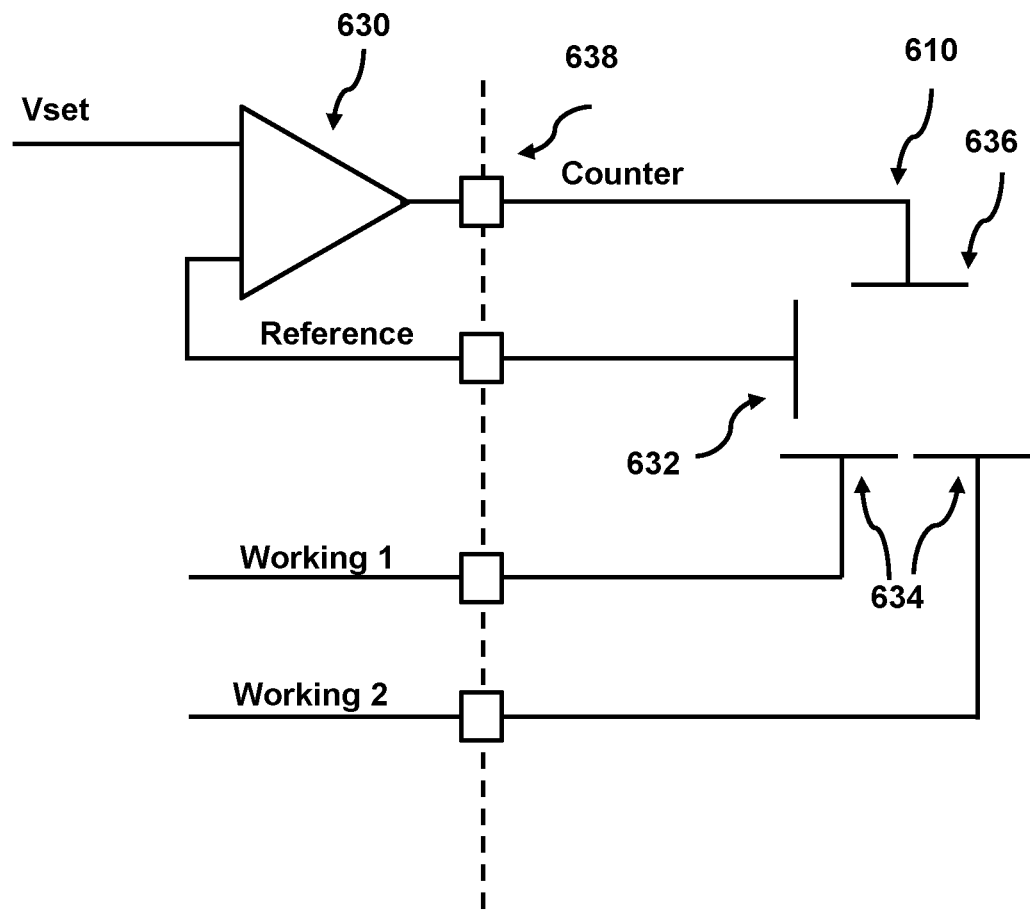
FIG. 6 illustrates an electronic block diagram of the sensor electrodes and a voltage being applied to the sensor electrodes, in accordance with one or more embodiments.

FIG. 6 illustrates an electronic block diagram of the sensor electrodes and a voltage being applied to the sensor electrodes according to an embodiment. In some embodiments, FIG. 6 may illustrate an electrode with a GOx sensor and/or an electrode capable of sensing GOx. For example, FIG. 6 may illustrate a working electrode with a GOx sensor that functions with a background electrode in which the background electrode has no GOx sensor (e.g., as discussed below in relation to FIGS. 8 and 9). The system may then compare the first signal and the second signal to detect ingestion of a medication by the user. The system may generate a sensor glucose value based on the comparison. In the embodiment illustrated in FIG. 6, an op amp 630 or other servo-controlled device may connect to sensor electrodes 610 through a circuit/electrode interface 638. The op amp 630, utilizing feedback through the sensor electrodes, attempts to maintain a prescribed voltage (what the DAC may desire the applied voltage to be) between a reference electrode 632 and a working electrode 634 by adjusting the voltage at a counter electrode 636. Current may then flow from a counter electrode 636 to a working electrode 634. Such current may be measured to ascertain the electrochemical reaction between the sensor electrodes 610 and the biomolecule of a sensor that has been placed in the vicinity of the sensor electrodes 610 and used as a catalyzing agent. The circuitry (e.g., processing circuitry) disclosed in FIGS. 7A, 7B, and 8 may be utilized in a long-term or implantable sensor or may be utilized in a short-term or subcutaneous sensor.

In a long-term sensor embodiment, where a GOx enzyme is used as a catalytic agent in a sensor, current may flow from the counter electrode 636 to a working electrode 634 only if there is oxygen in the vicinity of the enzyme and the sensor electrodes 610. Illustratively, if the voltage set at the reference electrode 632 is maintained at about 0.5 volts, the amount of current flowing from the counter electrode 636 to a working electrode 634 has a fairly linear relationship with unity slope to the amount of oxygen present in the area surrounding the enzyme and the electrodes. Thus, increased accuracy in determining an amount of oxygen in the blood may be achieved by maintaining the reference electrode 632 at about 0.5 volts and utilizing this region of the current-voltage curve for varying levels of blood oxygen. Different embodiments may utilize different sensors having biomolecules other than a glucose oxidase enzyme and may, therefore, have voltages other than 0.5 volts set at the reference electrode.

As discussed above, during initial implantation or insertion of the sensor 610, the sensor 610 may provide inaccurate readings due to the adjusting of the subject to the sensor and also electrochemical byproducts caused by the catalyst utilized in the sensor. A stabilization period is needed for many sensors in order for the sensor 610 to provide accurate readings of the physiological parameter of the subject. During the stabilization period, the sensor 610 does not provide accurate blood glucose measurements. Users and manufacturers of the sensors may desire to improve the stabilization timeframe for the sensor so that the sensors can be utilized quickly after insertion into the subject's body or a subcutaneous layer of the subject.

In previous sensor electrode systems, the stabilization period or timeframe was one hour to three hours. In order to decrease the stabilization period or timeframe and increase the timeliness of accuracy of the sensor, a sensor (or electrodes of a sensor) may be subjected to a number of pulses rather than the application of one pulse followed by the application of another voltage. for the second time period. In one embodiment, the first voltage may be 1.07 volts. In an embodiment, the first voltage may be 0.535 volts. In an embodiment, the first voltage may be approximately 0.7 volts.

Figure 7A:
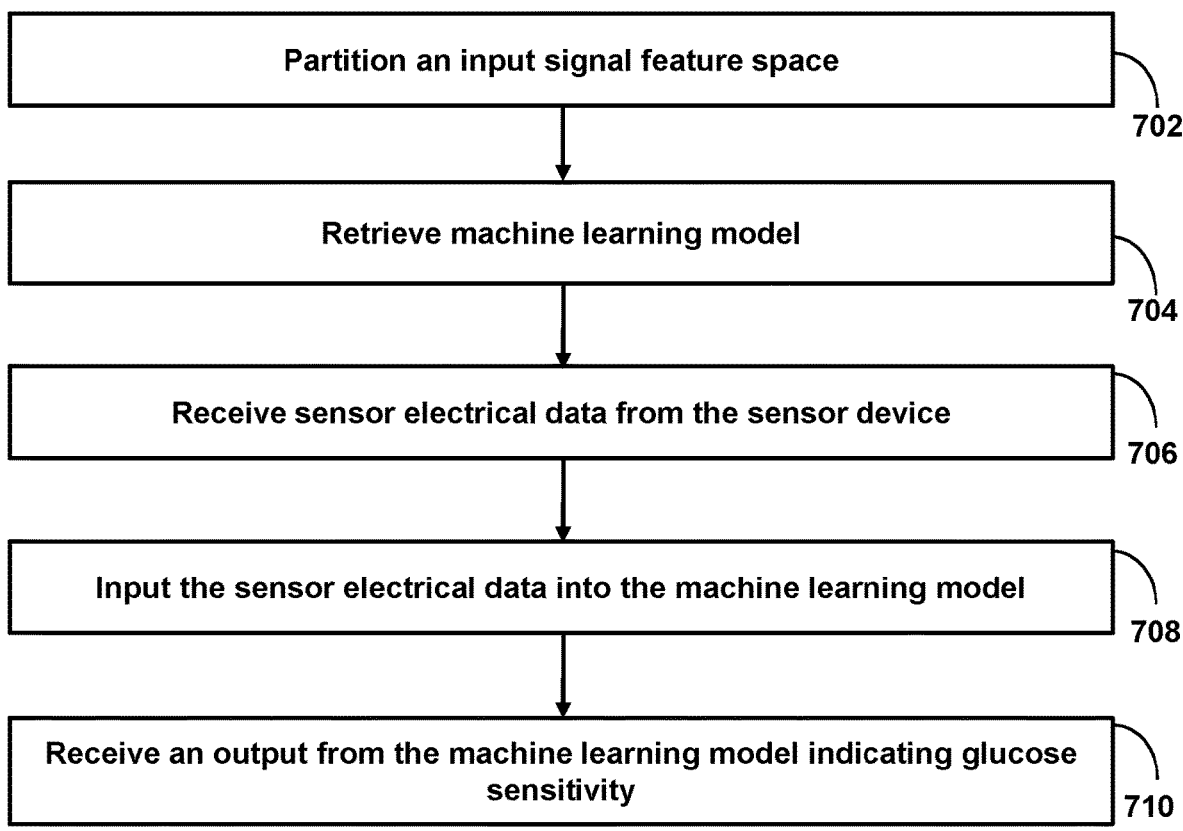
FIGS. 7A and 7B shows flowcharts of exemplary steps involved in modeling a relationship between glucose sensitivity and a sensor electrical property as a mosaic of models and training machine learning models to determine whether to blank sensor devices, in accordance with one or more embodiments.

FIG. 7A shows a flowchart of exemplary steps involved in modeling a relationship between glucose sensitivity and a sensor electrical property as a mosaic of models, in accordance with one or more embodiments. For example, process 700 may represent the steps taken by one or more devices as shown in FIGS. 2-6.

At step 702, process 700 (e.g., using any circuitry described in FIGS. 2-6) partitions an input signal feature space. For example, process 700 may partition the input signal feature space into a plurality of contiguous subspaces. The input signal feature space comprises data about how a sensor device interprets the complex relationship between measured sensor electrical properties and interstitial glucose values and may include information about glucose sensitivity and/or sensor electrical properties associated with the sensor device, one or more sensor features and a complex calibration factor that represents the relationship between each measured sensor electrical property and its associated contribution to the expressed glucose measurement value from the sensor, or another information about the sensor device or a relationship between a sensor electrical property and glucose sensitivity. The input sensor feature space may comprise the complex relationship between sensor electrical properties, as captured by measured sensor data and interstitial glucose values. In some embodiments, coefficients of sensor features in a mathematical model may represent the calibration factor that relates the corresponding sensor feature to the contribution that feature makes to the final calculated interstitial glucose value. In some embodiments, glucose sensitivity may be measured by an interstitial current signal ("Isig") or another glucose sensitivity measurement. In some embodiments, the sensor electrical property may include wear time, battery life, calibration information, or another sensor electrical property of the sensor device.

For example, process 700 may partition the input signal feature space according to certain ranges of the sensor electrical property for which glucose sensitivity behaves in a predicable manner. In some embodiments, process 700 may partition the input signal feature space according to sensor operating conditions (e.g., normal ranges, anomalous conditions, error states, etc.) based on signal characteristics (e.g., stability, regularity, consistency, etc.). Partitioning, for example, could result in one subspace associated with an operating condition characterized with typical analyte diffusion to the sensor and another subspace associated with reduced diffusion, which may be better served with a different glucose model. This partitioning may be created by partitioning the input signal feature space, by using sensor wear time and impedance. A complementary set of partitions may be defined through signal characteristics such as signals outside normal operating conditions or inconsistency in the signals.

At step 704, process 700 (e.g., using any circuitry described in FIGS. 2-6) retrieves a machine learning model. For example, for each subspace, the system may train a machine learning model to predict glucose sensitivity. In some embodiments, process 700 may select a machine learning model based on a determination that the machine learning model is the simplest model available that provides accurate results. For example, the models may be tested from simplest to most complex. The models may be tested based on one or more criteria, such as accuracy, percent error, bias, target metrics, or any other criteria. If a particular model does not pass the test (e.g., based on the one or more criteria), the system may test the next model (e.g., a more complex model). For example, each of the criteria above may be associated with a threshold. In some embodiments, not passing the test may comprise satisfying the threshold or not satisfying the threshold. The system may proceed until the simplest model that passes the test is selected. In some embodiments, the predicted glucose sensitivity may be based upon a range of values associated with the sensor electrical property for the subspace. In some embodiments, process 700 may train the machine learning model using training data comprising clinical data on glucose sensitivity. In some embodiments, the training data for each subspace may be partitioned according to the plurality of contiguous subspaces before being fed into the plurality of models. In some embodiments, the training data for each subspace may be weighted according to the plurality of contiguous subspaces.

At step 706, process 700 (e.g., using any circuitry described in FIGS. 2-6) receives sensor data from the sensor device. For example, the sensor device may provide sensor data on, for example, wear time, battery life, calibration information, electrical data, or other sensor electrical properties. At step 708, process 700 (e.g., using any circuitry described in FIGS. 2-6) inputs the sensor data into the machine learning model.

At step 710, process 700 (e.g., using circuitry described in FIGS. 2-6) receives an output from the machine learning model indicating glucose sensitivity of the sensor device. For example, the output may indicate a glucose sensitivity (e.g., glycemic range) of the sensor based on the sensor data. In some embodiments, process 700 may determine whether to blank the sensor based on the output from the machine learning model (e.g., as described below in relation to FIG. 10).

Figure 7B:
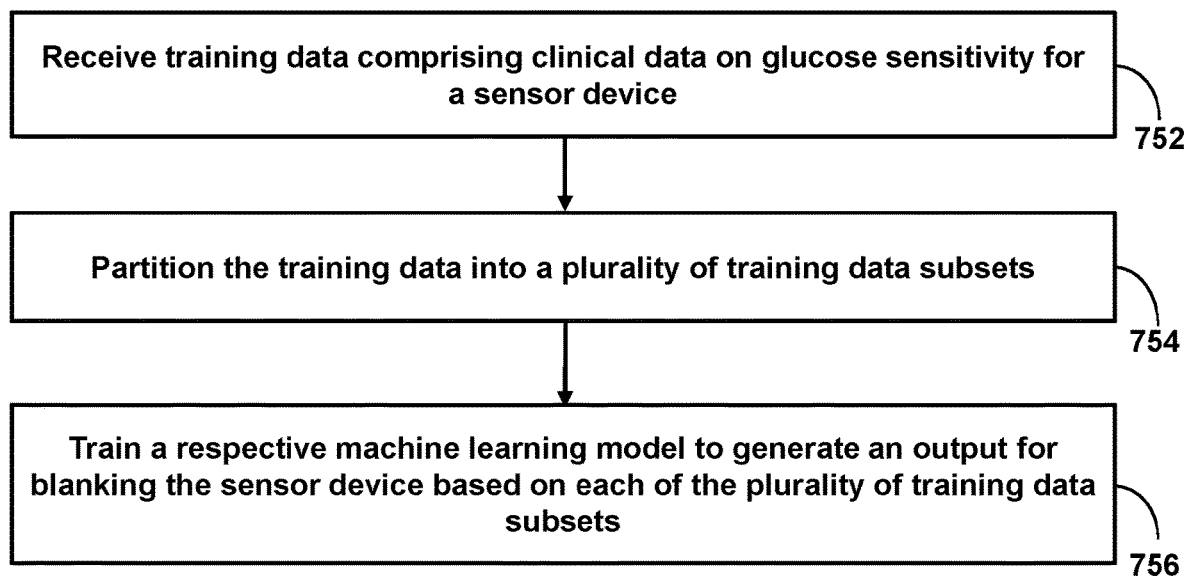

FIG. 7B shows a flowchart of exemplary steps involved in modeling a relationship between glucose sensitivity and a sensor electrical property as a mosaic of models, in accordance with one or more embodiments. For example, process 750 may represent the steps taken by one or more devices as shown in FIGS. 2-6.

At step 752, process 750 (e.g., using circuitry described in FIGS. 2-6) may receive training data comprising clinical data on glucose sensitivity for a sensor device. In some embodiments, the clinical data may correspond to a sensor electrical property of the sensor device. In some embodiments, the sensor electrical property may include wear time, battery life, calibration information, or another sensor electrical property of the sensor device. In some embodiments, the training data for each subspace may be weighted according to the plurality of contiguous subspaces.

At step 754, process 750 (e.g., using circuitry described in FIGS. 2-6) may partition the training data into a plurality of training data sets. In some embodiments, each of the plurality of training data subsets may correspond to one of a plurality of contiguous subspaces. In some embodiments, each of the plurality of contiguous subspaces may correspond to a range of values associated with the sensor electrical property for a respective subspace.

At step 756, process 750 (e.g., using circuitry described in FIGS. 2-6) may train a respective machine learning model of the plurality of machine learning models to generate an output for blanking the sensor device based on each of the plurality of training data subsets.

It is contemplated that the steps or descriptions of FIGS. 7A and 7B may be used with any other embodiment of this disclosure. In addition, the steps and descriptions described in relation to FIGS. 7A and 7B may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-5 and 8 could be used to perform one or more of the steps in FIG. 7A or 7B.

Figure 8:
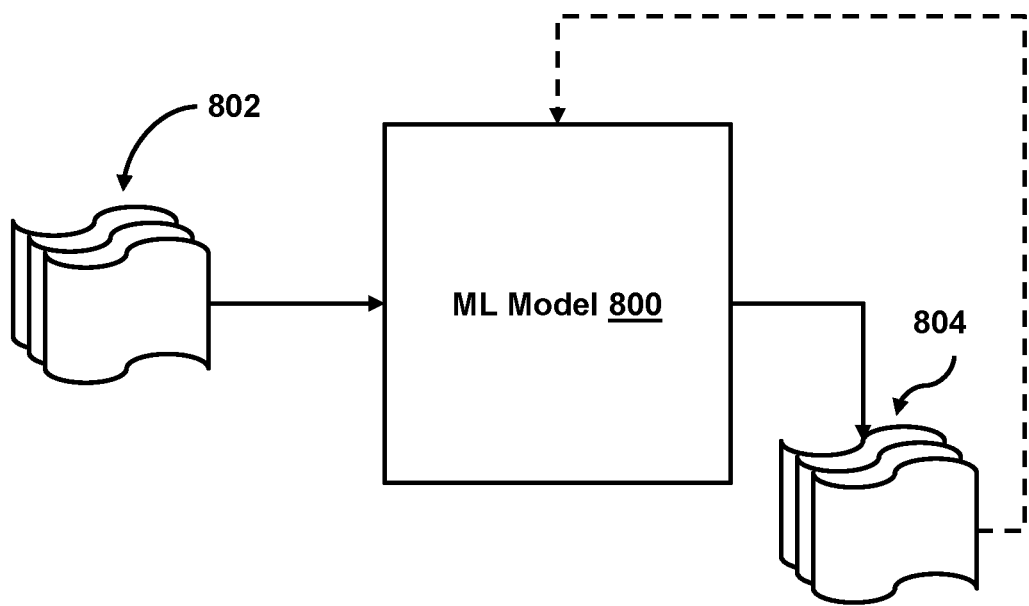
FIG. 8 shows an example machine learning model system for predicting glucose sensitivity based on sensor electrical properties of a sensor device, in accordance with one or more embodiments.

FIG. 8 shows a machine learning model system for predicting glucose sensitivity based on sensor electrical properties of a sensor device, in accordance with one or more embodiments.

In some embodiments, the machine learning model system may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

In some embodiments, the machine learning model system may update its configurations (e.g., weights, biases, or other parameters) based on its assessment of the predictions. Memory may store training data and one or more trained machine learning models.

As an example, a machine learning model 800 may take inputs 802 and provide outputs 804. In one use case, outputs 804 may be fed back (e.g., active feedback) to machine learning model 800 as input to train machine learning model 800 (e.g., alone or in conjunction with user indications of the accuracy of outputs 804, labels associated with the inputs 802, or with other reference feedback information). In another use case, machine learning model 800 may update its configurations (e.g., weights, biases, or other parameters) based on its assessment of its prediction (e.g., outputs 804) and reference feedback information (e.g., user indication of accuracy, reference labels, or other information). In another use case, where machine learning model 800 is a neural network, connection weights may be adjusted to reconcile differences between the neural network's prediction and the reference feedback. In a further use case, one or more neurons (or nodes) of the neural network may require that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 800 may be trained to generate better predictions.

In some embodiments, inputs 802 may comprise sensor data associated with one or more sensor electrical properties of a sensor device, and reference feedback information 804 (which feeds back into machine learning model 800 as inputs) may include clinical data on glucose sensitivity. In this embodiment, the sensor data input may include the sensor signals, reference glucose information, model output, calculations based on these values, and labeled clinical data. In some examples, the clinical data may be labeled for training purposes. For example, the labels may be based on stability, regularity, or other properties of the sensor signals. (e.g., labeled as compliant/non-compliant with iCGM criteria, normal, anomalous, erroneous, etc.). For example, by reviewing the sensor data and reference glucose information, a label may indicate conditions where a typical model output would exceed the iCGM criteria, or a label may indicate a region where the sensor is not responding appropriately to changing glucose. Accordingly, when a particular value associated with a sensor electrical property of a sensor device is provided as input 802 to machine learning model 800, machine learning model 800 may provide an output 804 including a prediction of glucose sensitivity of the sensor device.

In some embodiments, the system may partition the training data according to the same criteria used to partition the input signal feature space into a plurality of contiguous subspaces. For example, if the input signal feature space comprises twelve subspaces, the system may partition the training data into twelve subsets of data, producing one output estimate per subspace. In some embodiments, the system may partition the training data according to glucose sensitivity values, sensor features, or sensor electrical property values (e.g., according to the values used to partition the input signal feature space). In some embodiments, the partitioned training data may be used to train a model for each subspace, respectively.

In some embodiments, the entire training dataset may be used to train a model for each subspace, with the data corresponding to a particular subspace weighted more heavily when training that particular subspace. For example, the training data may be weighted according to the contiguous subspaces (e.g., based on the criteria used to partition the input signal feature space, as described above) and the training data corresponding to a particular subspace may be weighted more heavily when training a model for that particular subspace. In some examples, only the training dataset corresponding to a particular subspace will be used when training that particular subspace.

While machine learning model 800 is described in relation to the foregoing examples, it should be understood that machine learning model 800 may be trained to predict glucose sensitivity or any other quality of a sensor based on any sensor electrical property of a sensor device. In some embodiments, the outputs from machine learning model 800 may be utilized to determine whether to blank a signal (e.g., as described below in relation to FIGS. 9A and 9B).

Figure 9A:
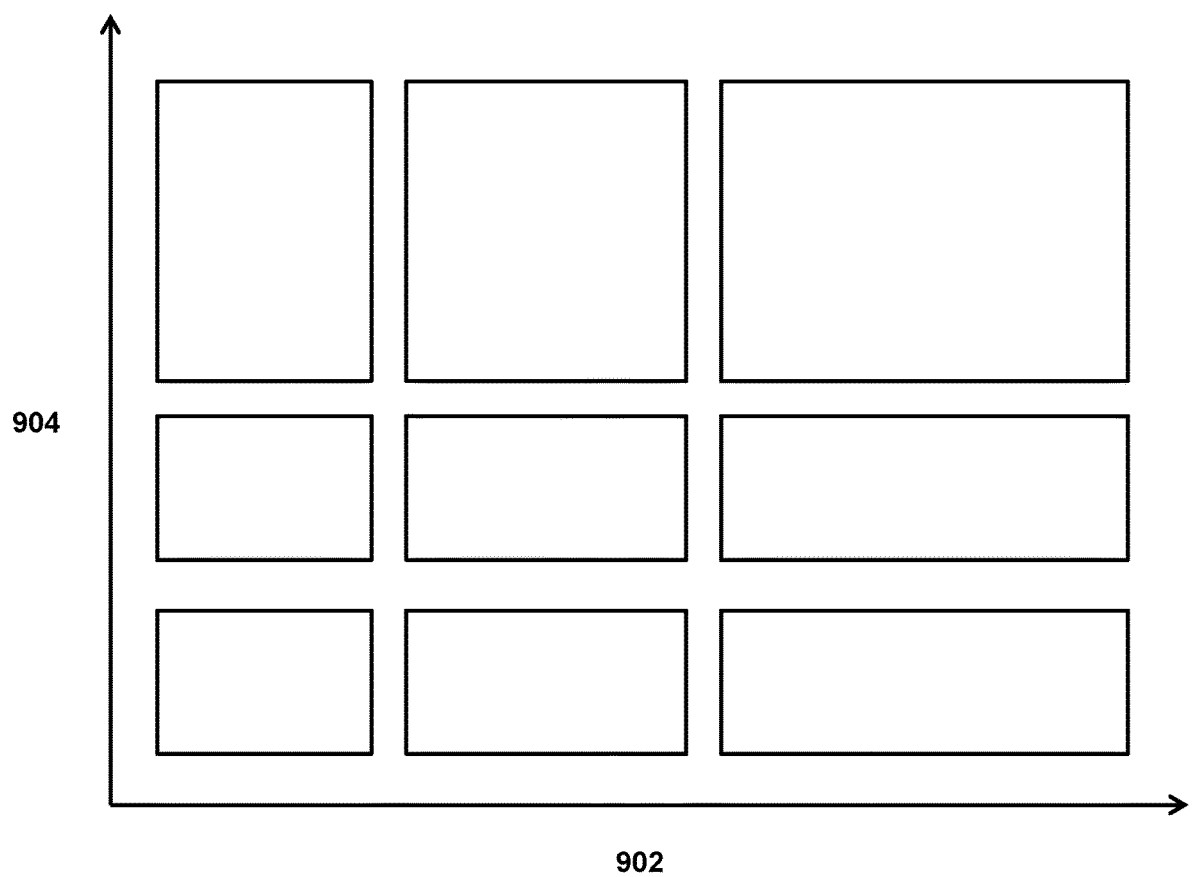
FIGS. 9A and 9B show example mosaics of models for modeling relationships between glucose sensitivity and a sensor electrical property as mosaics, in accordance with one or more embodiments.
Figure 9B:
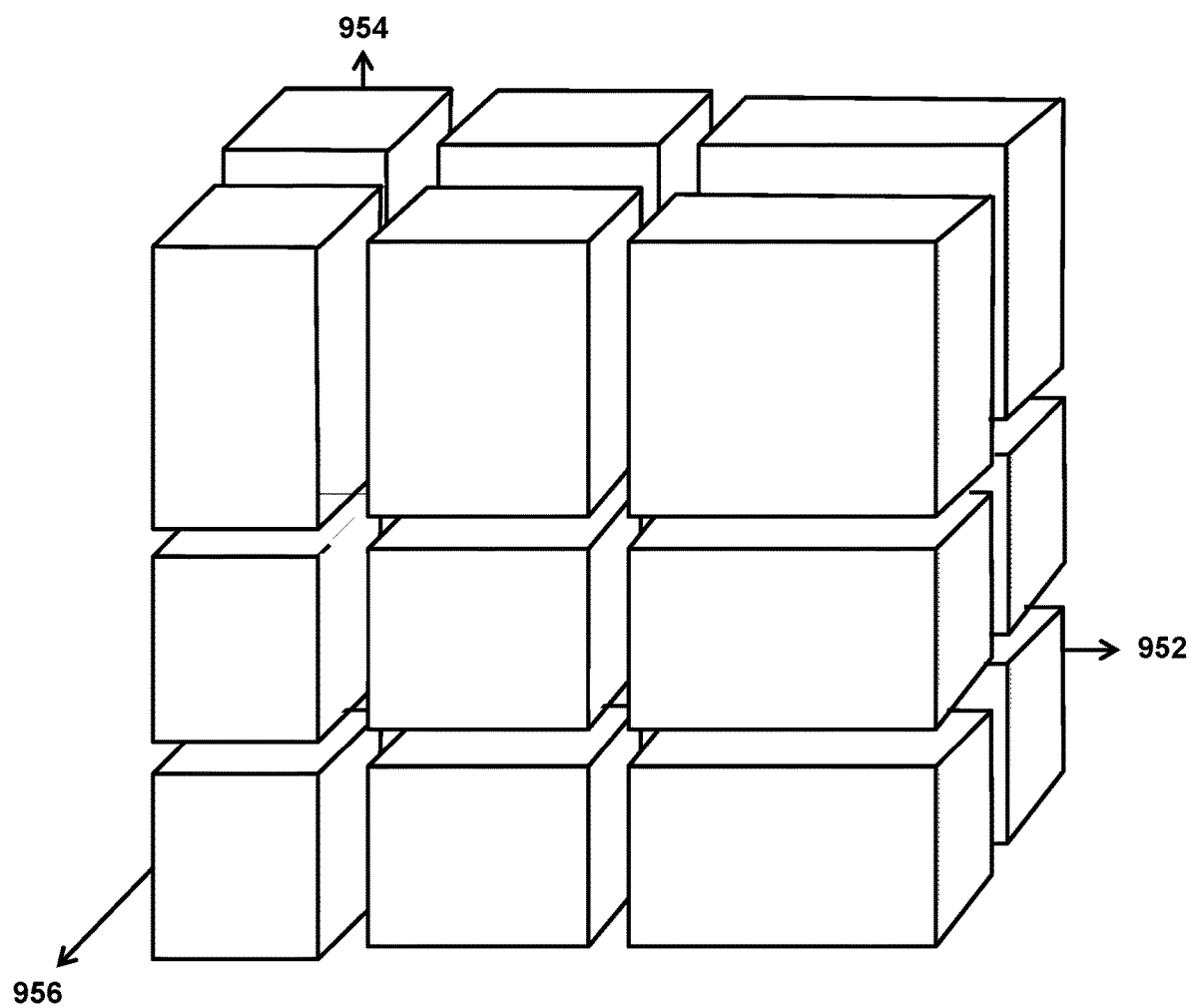

FIG. 9A shows a mosaic of models for modeling a relationship between glucose sensitivity and a sensor electrical property as a mosaic model 900, in accordance with one or more embodiments. FIG. 9B shows a mosaic of models for modeling a relationship between glucose sensitivity and two sensor electrical properties as a mosaic model 950, in accordance with one or more embodiments. In some embodiments, mosaic model 900, as shown in FIG. 9A, and mosaic model 950, as shown in FIG. 9B, may each comprise an input signal feature space. In some embodiments, the input signal feature space may comprise two or more dimensions.

As shown in FIG. 9A, axis 902 may represent a sensor electrical property or other sensor feature. For example, axis 902 may comprise wear time, battery life, or another measurement of time of a sensor device, calibration data of a sensor device, environmental properties (e.g., moisture) of a sensor device, or another sensor electrical property. In some embodiments, axis 904 may represent glucose sensitivity including but not limited to a maximum or minimum acceptable glucose measurement (e.g., based on iCGM criteria), a range of acceptable glucose measurements, a glycemic range, a calibration factor, or another measurement of glucose sensitivity.

As shown in FIG. 9B, axis 952 and axis 954 may each represent a sensor electrical property or other sensor feature. For example, axis 952 and axis 954 may each comprise one or wear time, battery life, or another measurement of time of a sensor device, calibration data of a sensor device, environmental properties (e.g., moisture) of a sensor device, or another sensor electrical property. In some embodiments, axis 956 may represent glucose sensitivity including but not limited to a maximum or minimum acceptable glucose measurement (e.g., based on iCGM criteria), a range of acceptable glucose measurements, a glycemic range, a calibration factor, or another measurement of glucose sensitivity. In some embodiments, these and other relationships may be modeled as a mosaic of models.

In some embodiments, the system may partition the input signal feature space to create mosaic model 900, as shown in FIG. 9A, or mosaic model 950, as shown in FIG. 9B. For example, the system may partition the input signal feature space into a plurality of contiguous subspaces. In some embodiments, to partition the input signal feature space, the system may identify subspaces of the input signal feature space within which glucose sensitivity behavior is the same or similar. For example, within certain ranges of the sensor electrical property (e.g., axis 902, axis 952, and axis 954), the glucose sensitivity may behave in a predictable manner (e.g., linear behavior or another predictable behavior). The system may therefore partition the input signal feature space according to such ranges of the sensor electrical property (e.g., axis 902, axis 952, and axis 954). In some aspects, the partitioning method is similar to clustering algorithms, where the features used for clustering result in multiple partitions or groups and where a single model dominates the output prediction. Therefore, unsupervised learning techniques, such as clustering algorithms may be used to create partitions using the described feature space. Other methods for identifying subspaces may be more accurate.

In some embodiments, to partition the input signal feature space, the system may identify stability of sensor trends, regularity of sensor signal magnitudes, or other characteristics of the sensor signal. Based on the aforementioned characteristics, the system may classify the sensor as normal, anomalous, erroneous, or another sensor operating condition. A normal operating condition may be one where a generic model performs well or where the model parameters match the general expectations. Conditions where the nearest model is biased, requires different predictors, or requires different predictor weights are commonly anomalous conditions. In contrast, erroneous operating conditions may be characterized with instability in the feature space components and high or unpredictable error in tuned models. The system may determine an optimal partition structure for each sensor classification. For example, the system may calculate improvements obtained from each partition structure in order to determine the optimal partition structure for the current application. The system may then partition the input signal feature space according to optimal partition structure. For example, the system may partition the input signal feature space as shown in FIGS. 9A and 9B or into another partition structure. Additionally, in some embodiments, the system may determine methods for handling error conditions identified within the error range of the operating conditions.

In some embodiments, subspace partitions may be overruled for various reasons. For example, if one or more subspaces output an erroneous glucose sensitivity (e.g., based on percent error, bias, target metrics, or any other criteria), the system may determine alternate partitions for increased accuracy. In some embodiments, the system may compare a model in a particular subspace to models in adjacent subspaces. If the system identifies discrepancies or gaps between models in adjacent subspaces, the system may overrule the partitions (e.g., determine alternate partitions). In some embodiments, the system may compare outputs from a model of a particular subspace to a composite model based on the models of the entire input signal feature space. If the system identifies discrepancies between the model of the particular subspace and the composite model, the system may overrule the partitions (e.g., determine alternate partitions).

In some embodiments, the system may use a variety of models for modeling the relationship between glucose sensitivity and the sensor electrical property or other sensor feature. In some embodiments, different models may be used in each subspace. The models may include a linear regression model, a neural network, a machine learning model, or any other model. For example, in some embodiments, a plurality of models that may be used may be ranked from simplest to most complex. In some embodiments, it may be advantageous to use a simpler model when possible. Therefore, the models may be tested from simplest to most complex. For example, simpler models (e.g., linear models) may comprise fewer variables while more complex models may comprise more variables. The models may be tested based on one or more criteria, such as accuracy, percent error, bias, target metrics, or any other criteria. If a particular model does not pass the test (e.g., based on the one or more criteria), the system may test the next model (e.g., a more complex model). For example, each of the criteria above may be associated with a threshold. In some embodiments, not passing the test may comprise satisfying the threshold or not satisfying the threshold. The system may proceed until the simplest model that passes the test is selected. This process may be performed for each subspace. In some embodiments, simpler models may be sufficient for certain subspaces while more complex models are necessary for other subspaces. Therefore, a combination of different models may be used.

In some embodiments, the system may use various smoothing or blending techniques between models of contiguous subspaces. For example, partition boundaries may experience abrupt changes in glucose sensitivity. In order to smooth or blend the glucose sensitivity outputs around the boundaries, the system may extend the model for each subspace into the adjacent subspaces by predicting outside the subspace boundaries and by using training data outside subspace boundaries. Therefore, the area surrounding the boundaries of the subspaces may comprise several overlapping models. In some embodiments, the system may build a composite model based on the models of the entire input signal feature space. The system may overlay the composite model on top of the models of each subspace (e.g., overlaying the entire input signal feature space) and blend the composite model with the models of each subspace. In some embodiments, the system may use other methods of smoothing or blending the glucose sensitivity outputs at the subspace boundaries.

Figure 10:
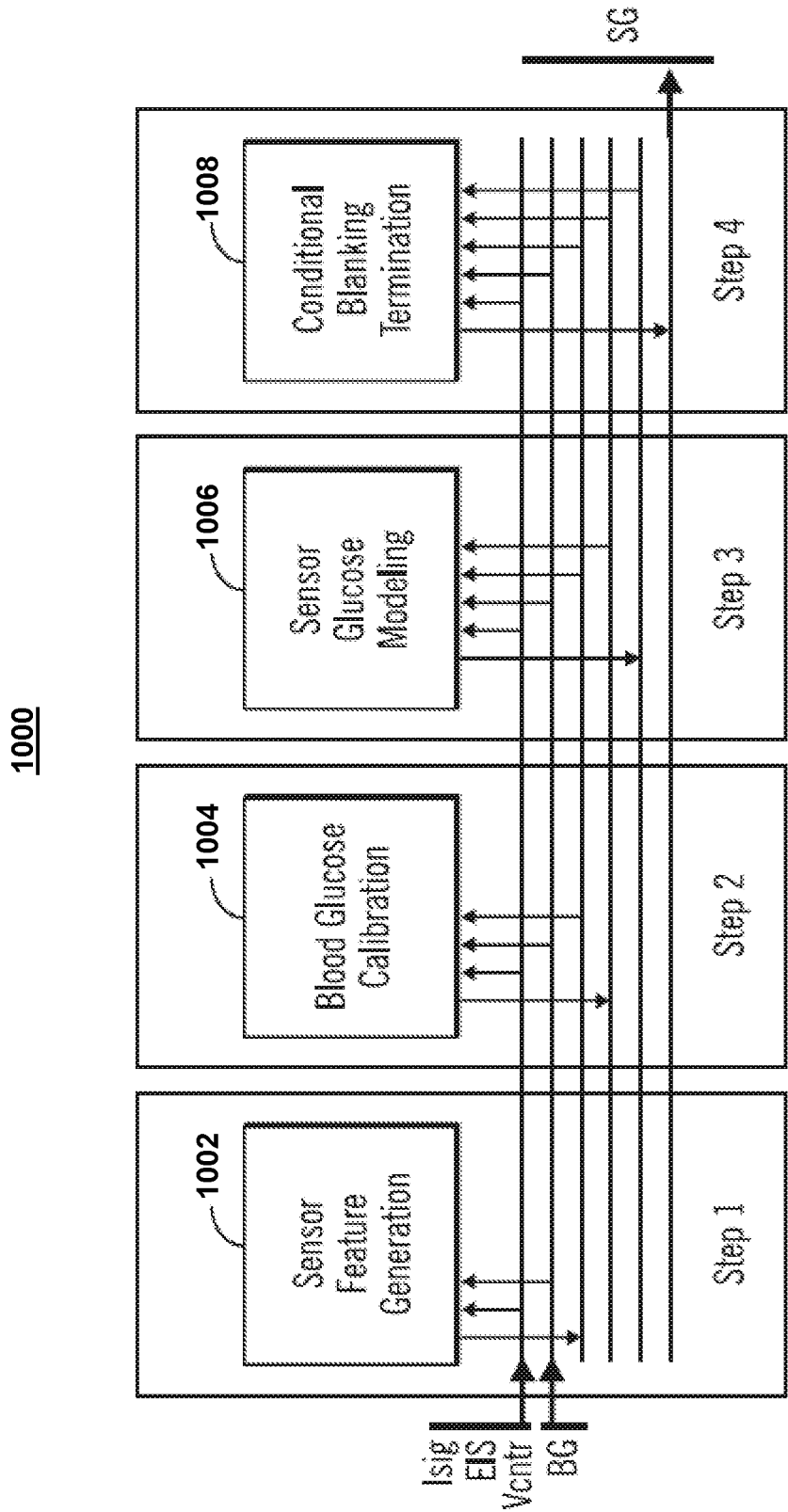
FIG. 10 shows a flow diagram for input data to be transformed to sensor glucose values, in accordance with one or more embodiments.

FIG. 10 shows a flow diagram 1000 for input data to be transformed to sensor glucose values, in accordance with one or more embodiments. As shown schematically in FIG. 10 the methods and systems herein include: a sensor feature generator 1002, a blood glucose calibrator 1004, a sensor glucose modeler 1006, and a conditional blanker and terminator 1008. In some embodiments, the sensor glucose modeler 1002 receives raw interstitial current signals, electrochemical impedance spectroscopy signals, and counter voltage signals and extracts the input features used by downstream machine learning models. The sensor glucose modeler 1006 is responsible for applying machine learning techniques to convert the input signals into sensor glucose values. The blood glucose calibrator 1004 is responsible for receiving input blood glucose values and adjusting the input sensor features from sensor glucose modeler 1002 accordingly. The conditional blanker and terminator 1008 applies various logic to determine when to stop displaying sensor output signals (e.g., remove, ignore, or forego to transmit the sensor data to the sensor device or any other device with a display interface) or terminate the sensor (e.g., stop transmitting sensor data from the sensor device) to reduce the probability of displaying noisy or erroneous information to the user or receiving output device. In some embodiments, input data (i.e., interstitially measured current (Isig), counter voltage (Vcntr), electrochemical impedance spectroscopy (EIS), and blood glucose calibration values (BG)) pass through the inventive algorithm to be transformed to sensor glucose values, or SG. The table below shows the information input and output from each of the four components.

Description of the Information Transfer

| Information Content | Component 1002 | Component 1004 | Component 1006 | Component 1008 |
|---|---|---|---|---|
| Input signals, Isig, Vcntr, EIS, BG | Input | N/A | N/A | Input |
| Base and Derivative Sensor Features Requiring No Calibration | Output | Input | Input | Input |
| Base and Derivative Sensor Features Requiring BG Calibration | N/A | Output | Input | Input |
| Initial Estimates of Sensor Glucose Values | N/A | N/A | Output | Input |
| Final Estimates of Sensor Glucose Values | N/A | N/A | N/A | Output |

The present invention improves upon current methods of sensor glucose modeler 1006. For example, the systems and methods described herein improve glucose sensitivity modeling by creating a mosaic of models of the relationship between glucose sensitivity and sensor electrical properties. The mosaic of models described herein may increase the accuracy of glucose sensitivity modeling.

In some embodiments, conditional blanker and terminator 1008 may include or be associated with machine learning model 800, as shown in FIG. 8. For example, machine learning model 800 may determine glucose sensitivity of a sensor device based on one or more sensor electrical properties (e.g., as described above with reference to FIG. 8). In some embodiments, acceptable ranges of glucose sensitivity of a sensor device may change as sensor electrical properties change. For example, as wear time of a sensor device increases, the sensitivity of the sensor device may decrease. The acceptable range of glucose sensitivity may therefore change dynamically with wear time (or another sensor electrical property). In some embodiments, glucose sensitivity may vary as sensor features change, for example, due to variability in the sensing environment, physiological dynamics, or sensor manufacturing. The mosaic of models described herein captures these dynamic changes and outputs a more accurate glucose sensitivity.

If a sensor device is not sufficiently sensitive for a particular sensor electrical property or sensor feature, the sensor device may be blanked. Conditional blanker and terminator 1008 may determine whether to blank the sensor data (e.g., from a display interface) based on the output from machine learning model 800. If the output from machine learning model 800 for a particular subspace indicates that the sensor device is not sufficiently sensitive (e.g., due to wear, time, calibration, sensing environment, physiological dynamics, sensor manufacturing, or other factors), conditional blanker and terminator 1008 may blank the sensor device. For example, conditional blanker and terminator 1008 may compare the output from machine learning model 800 with a glucose sensitivity threshold. If the output fails to satisfy the glucose sensitivity threshold, conditional blanker and terminator 1008 may blank the sensor device. If the output from machine learning model 800 indicates that the sensor device is sufficiently sensitive, conditional blanker and terminator 1008 may not blank the device. The mosaic of models within the input signal feature space may lead to more accurate outputs and therefore reduce the need for aggressive blanking and termination, allowing more precise blanking determination.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

1. A method comprising: partitioning an input signal feature space into a plurality of contiguous subspaces, the input signal feature space relating glucose sensitivity and a sensor electrical property associated with a sensor device; receiving, at the sensor device, sensor data relating to the sensor electrical property; for each subspace, inputting the sensor data into a machine learning model of a plurality of machine learning models based on a range of values associated with the sensor electrical property for the subspace, wherein each machine learning model of the plurality of machine learning models is trained using training data comprising clinical data on glucose sensitivity; and receiving an output from the machine learning model indicating glucose sensitivity.

2. The method of embodiment 1, further comprising determining whether to blank the sensor device based on the output from the machine learning model.

3. The method of embodiment 1 or 2, wherein glucose sensitivity is measured by an interstitial current signal ("Isig").

4. The method of any one of embodiments 1-3, wherein the sensor electrical property is wear time of the sensor device.

5. The method of any one of embodiments 1-4, further comprising determining the plurality of contiguous subspaces such that glucose sensitivity behavior, with respect to the sensor electrical property, is similar within each subspace.

6. The method of any one of embodiments 1-5, wherein the training data for each subspace is partitioned according to the plurality of contiguous subspaces.

7. The method of any one of embodiments 1-6, wherein the training data is weighted according to the plurality of contiguous subspaces.

8. The method of any one of embodiments 1-7, further comprising: determining a plurality of models including the machine learning model, wherein the models are ranked from simplest to most complex; testing each model of the plurality of models from simplest to most complex based on one or more criteria; and determining that the machine learning model is a simplest model that satisfies the one or more criteria.

9. A method comprising: receiving training data comprising clinical data on glucose sensitivity for a sensor device that corresponds to a sensor electrical property of the sensor device; partitioning the training data into a plurality of training data subsets, wherein each of the plurality of training data subsets corresponds to one of a plurality of contiguous subspaces, and wherein each of the plurality of contiguous subspaces corresponds to a range of values associated with the sensor electrical property for a respective subspace; and training a respective machine learning model to generate an output for blanking the sensor device based on each of the plurality of training data subsets.

10. The method of embodiment 9, wherein glucose sensitivity is measured by an interstitial current signal ("Isig").

11. The method of embodiment 9 or 10, wherein the sensor electrical property is wear time of the sensor device.

12. The method of any of embodiments 9-11, further comprising determining the plurality of contiguous subspaces such that glucose sensitivity behavior, with respect to the sensor electrical property, is similar within each subspace.

13. The method of any of embodiments 9-12, wherein blanking the sensor device comprises removing, ignoring, or foregoing to transmit sensor data to the sensor device.

14. The method of any of embodiments 9-13, wherein the training data is weighted according to the plurality of contiguous subspaces.

15. The method of any of embodiments 9-14, further comprising: determining a plurality of models including the machine learning model, wherein the models are ranked from simplest to most complex; testing each model of the plurality of models from simplest to most complex based on one or more criteria; and determining that the respective machine learning model is a simplest model that satisfies the one or more criteria.

16. A tangible, non-transitory, machine-readable medium storing instructions that, when executed by a data processing apparatus, cause the data processing apparatus to perform operations comprising those of any of embodiments 1-15.

17. A system comprising: one or more processors; and memory storing instructions that, when executed by the processors, cause the processors to effectuate operations comprising those of any of embodiments 1-15.

18. A system comprising means for performing any of embodiments 1-15.

What is claimed is:
1. A system comprising:
memory configured to store a plurality of machine learning models, wherein each machine learning model of the plurality of machine learning models is trained using training data comprising clinical data on glucose sensitivity; and
one or more processors configured to:
partition an input signal feature space into a plurality of contiguous subspaces, the input signal feature space relating glucose sensitivity and a sensor electrical property associated with a glucose sensor device, each subspace of the plurality of contiguous subspaces associated with a respective glucose sensitivity behavior of the glucose sensor device that is modeled by a respective machine learning model in the plurality of machine learning models;
receive sensor data relating to the sensor electrical property;
input the sensor data into a machine learning model of the plurality of machine learning models, wherein the machine learning model is selected from the plurality of machine learning models based on the sensor data and a respective range of values associated with the sensor electrical property for each subspace of the plurality of contiguous subspaces;
receive an output from the machine learning model indicating the glucose sensitivity of the glucose sensor device;
determine a glucose level based on the sensor data and the glucose sensitivity; and control delivery of insulin by an insulin delivery device based on the determined glucose level.

2. The system of claim 1, wherein the one or more processors are further configured to, based on the output from the machine learning model and one or more criteria:
blank the glucose sensor device when the output from the machine learning model is noncompliant with the one or more criteria; or
utilize readings from the glucose sensor device for glucose level monitoring or glucose level management when the output from the machine learning model is compliant with the one or more criteria.

3. The system of claim 1, wherein the glucose sensitivity is measured based on an interstitial current signal.

4. The system of claim 1, wherein the sensor electrical property includes wear time of the glucose sensor device.

5. The system of claim 1, wherein, to partition the input signal feature space, the one or more processors are further configured to determine the plurality of contiguous subspaces such that the glucose sensitivity, with respect to the sensor electrical property, behaves in a same manner within each subspace of the plurality of contiguous subspaces.

6. The system of claim 1, wherein the training data for each machine learning model of the plurality of machine learning models is partitioned according to the plurality of contiguous subspaces.

7. The system of claim 1, wherein the training data is weighted according to the plurality of contiguous subspaces.

8. The system of claim 1, wherein the one or more processors are further configured to:
obtain a plurality of models including the machine learning model, wherein the plurality of models are ranked from simplest to most complex;
test each model of the plurality of models from simplest to most complex based on one or more criteria; and
determine that the machine learning model is a simplest model that satisfies the one or more criteria.

9. The system of claim 1, wherein partitioning the input signal feature space into the plurality of contiguous subspaces comprises partitioning the input signal feature space based on ranges of the sensor electrical property, sensor operating conditions, or a combination thereof.

10. The system of claim 9, wherein the sensor electrical property and sensor operating conditions include wear time, battery life, calibration data, environmental property, a maximum or minimum acceptable glucose measurement, a range of acceptable glucose measurements, a glycemic range, a calibration factor, or a combination thereof.

11. A method comprising, by one or more processors:
partitioning an input signal feature space into a plurality of contiguous subspaces, the input signal feature space relating glucose sensitivity and a sensor electrical property associated with a glucose sensor device, each subspace of the plurality of contiguous subspaces associated with a respective glucose sensitivity behavior of the glucose sensor device that is modeled by a respective machine learning model of a plurality of machine learning models;
receiving sensor data relating to the sensor electrical property;
inputting the sensor data into a machine learning model of the plurality of machine learning models, wherein the machine learning model is selected from the plurality of machine learning models based on the sensor data and a respective range of values associated with the sensor electrical property for each subspace of the plurality of contiguous subspaces, wherein each machine learning model of the plurality of machine learning models is trained using training data comprising clinical data on glucose sensitivity;
receiving an output from the machine learning model indicating the glucose sensitivity of the glucose sensor device;
determining a glucose level based on the sensor data and the glucose sensitivity; and
controlling an insulin delivery device to deliver insulin based on the determined glucose level.

12. The method of claim 11, further comprising, based on the output from the machine learning model and one or more criteria:
blanking the glucose sensor device when the output from the machine learning model is noncompliant with the one or more criteria; or
utilizing readings from the glucose sensor device for glucose level monitoring or glucose level management when the output from the machine learning model is compliant with the one or more criteria.

13. The method of claim 11, wherein the glucose sensitivity is measured based on an interstitial current signal ("Isig").

14. The method of claim 11, wherein the sensor electrical property includes wear time of the glucose sensor device.

15. The method of claim 11, further comprising determining the plurality of contiguous subspaces such that the glucose sensitivity, with respect to the sensor electrical property, behaves in a same manner within each subspace of the plurality of contiguous subspaces.

16. The method of claim 11, wherein the training data for each machine learning model of the plurality of machine learning models is partitioned according to the plurality of contiguous subspaces.

17. The method of claim 11, wherein the training data is weighted according to the plurality of contiguous subspaces.

18. The method of claim 11, further comprising:
obtaining a plurality of models including the machine learning model, wherein the plurality of models are ranked from simplest to most complex;
testing each model of the plurality of models from simplest to most complex based on one or more criteria; and
determining that the machine learning model is a simplest model that satisfies the one or more criteria.

19. A non-transitory computer-readable medium storing instructions that, when executed by one or more processors, cause performance of operations comprising:
partitioning an input signal feature space into a plurality of contiguous subspaces, the input signal feature space relating glucose sensitivity and a sensor electrical property associated with a glucose sensor device, each subspace of the plurality of contiguous subspaces associated with a respective glucose sensitivity behavior of the glucose sensor device that is modeled by a respective machine learning model in a plurality of machine learning models;
receiving sensor data relating to the sensor electrical property;
inputting the sensor data into a machine learning model of the plurality of machine learning models, wherein the machine learning model is selected from the plurality of machine learning models based on the sensor data and a respective range of values associated with the sensor electrical property for each subspace of the plurality of contiguous subspaces, wherein each machine learning model of the plurality of machine learning models is trained using training data comprising clinical data on glucose sensitivity;

receiving an output from the machine learning model indicating the glucose sensitivity of the glucose sensor device;

determining a glucose level based on the sensor data and the glucose sensitivity; and controlling an insulin delivery device to deliver an amount of insulin based on the determined glucose level.

20. The non-transitory computer-readable medium of claim 19, wherein the operations further comprise, based on the output from the machine learning model and one or more criteria:

blanking the glucose sensor device when the output from the machine learning model is noncompliant with the one or more criteria; or utilizing readings from the glucose sensor device for glucose level monitoring or glucose level management when the output from the machine learning model is compliant with the one or more criteria.

\* \* \* \* \*